ST. AUGUSTINEGRASS

Filed May 8, 1967

INVENTOR
John A. Long
by Strauch, Nolan, Neale, Nies & Kurz
ATTORNEYS

United States Patent Office

Plant Pat. 2,863
Patented Feb. 18, 1969

2,863
ST. AUGUSTINE GRASS

John A. Long, Marysville, Ohio, assignor to The O. M. Scott & Sons Company, Marysville, Ohio, a corporation of Ohio Filed May 8, 1967, Ser. No. 637,014
U.S. Cl. Plt.—88 1 Claim
Int. Cl. A01h 5/12

ABSTRACT OF THE DISCLOSURE

A variety of perennial St. Augustine grass having outstanding resistance to chinch bugs, a pleasing, moderate olive green color, and a fine leaf texture. The variety is highly competitive with weeds, easily propagated, vigorous, rugged, tolerant to commercial pesticides, and has a high rate of horizontal growth.

*Summary of the variety*

This invention relates to a new and distinct variety of perennial St. Augustine grass plant originated by progeny selection from a heterozygous population cultivated under greenhouse conditions. The original plant material was vegetatively propagated by stolons and installed in field plots for evaluation. This St. Augustine grass was labeled Ea 611081.

Ea 611081 St. Augustine grass has several distinctive characteristics not evident in other St. Augustine grasses. The most desirable of these is its outstanding resistance to chinch bug damage. Others are good competitiveness with weeds in turfs in which it is planted, a pleasing moderate olive green color similar to that of Bitter Blue St. Augustine grass, ease of propagation, fine leaf texture, vigor, high degree of tolerance to commercial pesticides, and energetic horizontal growth, which makes the fast establishment of a new lawn possible.

The aforementioned desirable and unique qualities make Ea 611081 St. Augustine grass an outstanding turfgrass. Because of its vigor of growth and competitiveness, it makes a dense, rugged turf with good traffic wearing qualities. Furthermore, its high density provides a desirable cushionlike resilience.

Ea 611081 St. Augustine grass provides an aesthetic turf from a color standpoint. Additionally, its fine leaf texture imparts a desirable carpetlike quality and appearance to the turf.

The outstanding resistance of Ea 611081 St. Augustine grass to chinch bug damage contributes materially to its excellent performance. This characteristic is of importance to subsequent vigor of the plant throughout the season. The inherent resistance to chinch bug damage also extends the season of grass enjoyment and lessens the maintenance procedures and costs of providing insecticides for protecting against these insects.

It is my primary object to provide a St. Augustine grass plant having the desirable characteristics mentioned above and described in detail below. Other objects will become apparent to those skilled in the relevant arts from the appended claim and from the following description in conjunction with the accompanying illustrations of Ea 611081 St. Augustine grass.

*Brief description of the illustrations*

Figure 1:
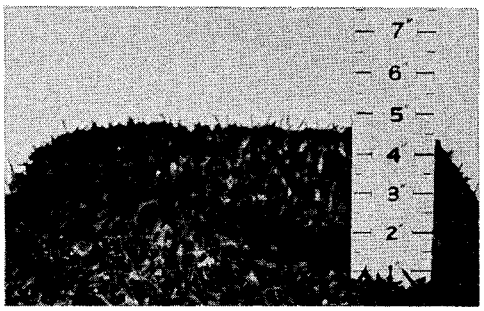
Figure 2:
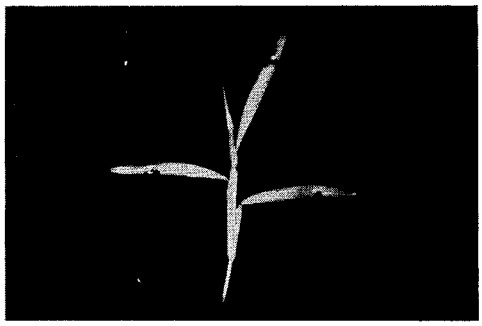
Figure 3:
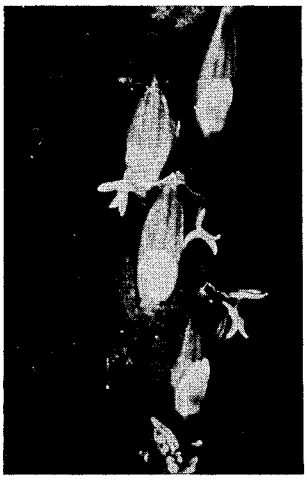

FIGURE 1 is a picture of Ea 611081 St. Augustine turf showing generally the characteristics of this new variety;

FIGURE 2 shows the leaves and stem of an Ea 611081 St. Augustine grass plant; and FIGURE 3 shows the stigma color and spikelet characteristics of Ea 611081 St. Augustine grass.

*Detailed description of the variety*

Ea 611081 St. Augustine grass (*Stenotaphrum secundatum*) is distinguished from the widely grown Texas common St. Augustine grass by its stigma color in that Ea 611081 St. Augustine grass has a purple stigma while Texas common St. Augustine grass has white stigmas. The chromosome numbers and stigma colors of Ea 611081 and other St. Augustine grasses are compared in Table 1.

TABLE 1.—CHROMOSOME NUMBERS AND STIGMA COLOR OF Ea 611081 ST. AUGUSTINE GRASS AND OTHER ST. AUGUSTINE GRASSES

| Selection/variety | Chromosome No. (unreduced)[1] | Stigma color |
|---|---|---|
| Ea 611081 | 18 | Purple. |
| PI 243552[2] | 18 | Do. |
| Texas common | 18 | White. |
| Floratine | 27 | Purple. |
| Variegatum | 18 | Do. |
| Bitter blue | 27 | Do. |

[1] Chromosome number determinations were made on pollen mother cells and root tip cells.
[2] PI is the prefix letter designation assigned accessions that are collected by the Plant Introduction section of the United States Department of Agriculture.

Ea 611081 has a moderate olive green color[1] as mentioned above. The culms of Ea 611081 are compressed and branched. The flowering shoots are 5 to 16 centimeters tall. Blades are generally less than 6 centimeters long and 7 to 7.5 millimeters wide. Racemes are 5 to 10 centimeters long. Spikelets are solitary or in pairs 3.2 to 3.3 millimeters long. The first glume is 1.07 to 1.11 millimeters long, the second glume 3.00 to 3.06 millimeters long, the palea 2.96 to 3.02 millimeters long, and the lemma 3.09 to 3.39 millimeters long.

Since environmental conditions such as climate and soil influence morphological characteristics to some degree, the morphological characteristics may vary slightly from locale to locale.

Morphological characteristics of Ea 611081 St. Augustine grass are compared to those of Floratine and Bitter Blue St. Augustine grasses in Table 2.

TABLE 2.—COMPARATIVE LEAF BLADE WIDTH AND LENGTH FOR Ea 611081 AND OTHER ST. AUGUSTINE GRASSES

| Selection/variety | Leaf blade width (mm.)[1] | Leaf blade length (mm.) |
|---|---|---|
| Ea 611081 | [2] 7.10–7.50 | [2] 58.47–61.53 |
| Floratine | 7.28–7.72 | 60.99–64.61 |
| Bitter blue | 7.41–7.79 | 77.26–79.74 |

[1] Leaf blade width recorded one inch from leaf collar.
[2] Where Ea 611081 plants are maintained as a turf, the range of leaf blade length and width may not vary as much as indicated.

The horizontal growth rate of Ea 611081 St. Augustine grass, as reflected in rate of establishment, is significantly higher than those of Texas common, Floratine, and PI 243552 varieties of St. Augustine grass. This was found to be true for widely separated geographical areas. The horizontal growth rate of Ea 611081 is compared with

[1] The ISCC–NBS method of designating colors described in National Bureau of Standards Circular No. 553. The designated color is that of plants grown under greenhouse conditions.

the growth rates of Texas common, Floratine, and PI 243552 in Tables 3 and 4.

TABLE 3.—RELATIVE COMPARISON OF PERCENT TURF COVER OF Ea 611081 ST. AUGUSTINE GRASS AND TEXAS COMMON ST. AUGUSTINE GRASS AT ROSENBERG, TEXAS

| Selection/variety: | Percent area covered |
|---|---|
| Ea 611081 | 80 |
| Texas common | 67 |
| LSD 10% | 11 |

TABLE 4.—RELATIVE COMPARISON OF PERCENT TURF COVER OF Ea 611081 ST. AUGUSTINE GRASS, FLORATINE, AND PI 243552 ST. AUGUSTINE GRASSES AT APOPKA, FLORIDA

| | Date | | | |
|---|---|---|---|---|
| | 8-16 | | 10-17 | |
| | Percent area covered | | | |
| Selection/variety | T | UT | T | UT |
| Ea 611081 | 73 | 40 | 95 | 73 |
| PI 243552 | 33 | 23 | 57 | 45 |
| Floratine | 40 | 23 | 57 | 47 |
| LSD 5% | 23 | NS | 20 | 16 |

T=plots treated with nematocide; UT=plots not treated with nematocide.

The data in Table 5 shows the low level of chinch bug infestation in plots of Ea 611081 St. Augustine grass as compared to the level in plots of Floratine St. Augustine grasses in the same locale. Ratings on damage are also given in the table. Table 6 compares the chinch bug populations of and turf damage to Ea 611081 and other St. Augustine grasses in tests conducted during a different growing season. Again, all plots were in the same locale.

TABLE 5.—CHINCH BUG POPULATIONS AND TURF DAMAGE CAUSED BY CHINCH BUGS TO Ea 611081 ST. AUGUSTINE GRASS AND FLORATINE ST. AUGUSTINE GRASS AT APOPKA, FLORIDA

| Selection/variety | Chinch bug population [1] | Turf damage [2] |
|---|---|---|
| Ea 611081 | 2.3 | 1.7 |
| Floratine | 25.0 | 5.3 |
| LSD 5% | 11 | |

[1] Chinch bug counts per ⅔ square foot.
[2] Turf damage: 10-turf completely killed to 1-no visible injury to turf.

TABLE 6.—CHINCH BUG POPULATIONS ON AND TURF DAMAGE CAUSED BY CHINCH BUGS TO Ea 611081 ST. AUGUSTINE GRASS AND OTHER ST. AUGUSTINE GRASSES AT APOPKA, FLORIDA

| Selection/variety | Chinch bug population [1] | Turf damage [2] | Turf quality |
|---|---|---|---|
| Ea 611081 | 11 | 1.0 | Good. |
| PI 243552 | 126 | 9.0 | Very poor. |
| Floratine | 47 | 5.0 | Poor. |
| Florida #40 | 58 | 7.0 | Very poor. |
| Belle Glade #1 | 70 | 8.0 | Do. |
| Belle Glade #2 | 65 | 6.0 | Poor. |
| Variegatum | 89 | 8.0 | Very poor. |

[1] Chinch bug counts per ⅔ square foot.
[2] Turf damage: 10-turf completely killed to 1-no visible turf injury.

Ea 611081 St. Augustine grass reproduces and propagates vegetatively by propagules. This results in the production of uniform plants retaining the parental characteristics. Ea 611081 does produce seed, but only in very limited amounts. It is accordingly not practical to reproduce Ea 611081 by seed.

What is claimed and desired to be secured by Letters Patent is:

1. A variety of St. Augustine grass plant, substantially as shown and described herein, characterized particularly by resistance to chinch bug damage, vigorous horizontal growth, fine leaf texture, good color and ease of propagation.

No references cited.

ROBERT E. BAGWILL, *Primary Examiner.*